United States Patent [19]

Verdiccio et al.

[11] 4,138,371

[45] Feb. 6, 1979

[54] WASHING METHOD USING AMPHOTERIC SURFACE ACTIVE AGENTS

[75] Inventors: Robert J. Verdiccio, Succasunna, N.J.; Louis J. Nehmsmann, Ellicott City, Md.

[73] Assignee: GAF Corporation, New York, N.Y.

[21] Appl. No.: 822,703

[22] Filed: Aug. 8, 1977

Related U.S. Application Data

[60] Division of Ser. No. 674,442, Apr. 7, 1976, which is a continuation-in-part of Ser. No. 561,673, Mar. 25, 1975, abandoned, which is a continuation of Ser. No. 349,560, Apr. 9, 1973, abandoned.

[51] Int. Cl.² ............................................. C11D 1/12
[52] U.S. Cl. .................................. 252/545; 252/117; 252/547; 252/548; 252/DIG. 7; 252/DIG. 13; 252/DIG. 14; 252/DIG. 16; 260/458 C; 260/459 R; 424/70
[58] Field of Search ........ 252/545, DIG. 7, DIG. 13, 252/DIG. 14; 260/458 R, 459 A, 458 C; 424/70

[56] References Cited

U.S. PATENT DOCUMENTS

| | | |
|---|---|---|
| 3,055,836 | 9/1962 | Masci et al. ........................ 252/545 |
| 3,198,815 | 8/1965 | Mannheimer et al. ............. 260/401 |
| 3,769,311 | 10/1973 | Armstrong .......................... 260/549 |
| 3,925,262 | 12/1975 | Laughlin et al. ................... 252/526 |
| 3,928,251 | 12/1975 | Bolich et al. ....................... 252/545 |
| 3,950,417 | 4/1976 | Verdicchio ......................... 252/545 |

FOREIGN PATENT DOCUMENTS

| | | |
|---|---|---|
| 813502 | 10/1974 | Belgium. |
| 1617691 | 10/1970 | Fed. Rep. of Germany. |
| 2353860 | 5/1974 | Fed. Rep. of Germany. |
| 2341592 | 2/1975 | Fed. Rep. of Germany. |
| 1293265 | 4/1962 | France. |
| 355457 | 8/1961 | Switzerland. |
| 465200 | 4/1937 | United Kingdom. |

*Primary Examiner*—P.E. Willis, Jr.
*Attorney, Agent, or Firm*—W. C. Kehm; J. J. Ward; A. Dresner

[57] ABSTRACT

Compounds having the formula

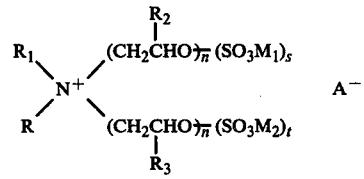

wherein R represents a $C_8$–$C_{14}$ aliphatic radical; $R_1$ represents a $C_1$–$C_4$ lower alkyl radical; $R_2$ and $R_3$ each represent H or $CH_3$; $M_1$ and $M_2$ represent cations of hydrogen, ammonium, alkyl ammonium, alkali metal, or an equivalent of alkaline earth metal; n is an integer having an average value of from 5 to 10; s and t can either be 0 or 1 but both cannot be simultaneously 0; and A represents an anionic radical such as hydroxide, halogen, sulfate, alkyl sulfate, etc. are useful as essentially non-iritating and high foaming amphoteric surface active agents for shampoo and other cosmetic applications. Preferably R is a naturally derived or synthetic alkyl group containing 10–12 carbon atoms.

13 Claims, No Drawings

4,138,371

WASHING METHOD USING AMPHOTERIC SURFACE ACTIVE AGENTS

CROSS-REFERENCE TO RELATED APPLICATIONS

This is a division of application Ser. No. 674,442, filed Apr. 7, 1976, which is a continuation-in-part of application Ser. No. 561,673, filed Mar. 25, 1975 and now abandoned which in turn was a continuation of application Ser. No. 349,560 filed Apr. 9, 1973 and also now abandoned.

BACKGROUND OF THE INVENTION

1. Field of the Invention

This invention relates to new amphoteric surfactants, and more particularly to specific ethoxylated amines which are quaternized and partially sulfated; methods of making same and to methods of use therefor. More particularly, this invention relates to novel derivatives of certain amphoteric, water-soluble compounds that are characterized by the following formula

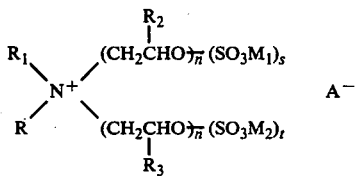

wherein R represents a $C_8$–$C_{14}$ aliphatic radical; $R_1$ represents a $C_1$–$C_4$ lower alkyl radical; $R_2$ and $R_3$ each represent H or $CH_3$; $M_1$ and $M_2$ represent cations of hydrogen, ammonium, alkyl ammonium, alkali metal, or an equivalent of alkaline earth metal; $n$ is an integer having an average value of from 5 to 10; $s$ and $t$ can either be 0 or 1 but both cannot be simultaneously 0; and A represents an anionic radical such as hydroxide, halogen, sulfate, alkyl sulfate, etc. Such derivatives are useful as essentially non-irritating and high foaming amphoteric surface active agents for shampoo and other cosmetic applications. Preferably, R in such derivative is a naturally derived or a synthetic alkyl group containing an average of 10–12 carbon atoms.

2. Description of the Prior Art

The prior art describes many varied types of amine sulfonates, sulfates and related compounds. For example, hydroxy alkyl and dihydroxy alkyl derivatives of higher fatty acid amines have been sulfated with chlorosulfonic acid to yield the sulfate. However, none of these compounds have achieved significant commercial acceptance and in none are found all of the desirable properties of the instant invention.

Also known in the art, as, e.g. from U.S. Pat. No. 2,185,163 are polyoxyalkylene ammonium compounds, formed from reaction at elevated temperatures of tertiary amine oxides with alkylene oxides in the presence of water, and such compounds are useful as wetting and emulsifying agents. However, these known materials do not have the capacity to be high foaming and simultaneously non-irritating to the hair, skin, and eyes as is characteristic of the present invention.

While the common soaps are inexpensive and good cleansing agents, they have certain undesirable characteristics, among which are: poor foamability and cleaning in hard water; when used for shampooing, which is the most preferred embodiment of this invention, they sometimes form insoluble salts which deposit on the hair, thereby imparting a dull appearance thereto, and generally require rinses of acidic nature for their removal; they are irritating to the eyes; tend to precipitate at pH values of 7 or below; and foam poorly at pH values of 6–7.

While the amides of said amino acids do exhibit better resistance to hard water when compared with common soaps, they exhibit poor foam and poor foam stability in hard water; they dull hair as do the common soaps but to a lesser extent when used as shampoos and they precipitate out in aqueous media at pH 4.5.

SUMMARY OF THE INVENTION

It has been found, in the preferred embodiments of this invention, that the quaternized and sulfated ethoxylated amine compositions according to the instant invention comprise very valuable surface-active agents which may be used either alone or admixed with other cationic, anionic or non-ionic surface active agents in the different fields above referred to, and most preferably for shampooing the hair.

The instant compositions comprise a very valuable group of surface-active agents, known as amphoteric compounds, i.e., chemical agents containing both cationic and anionic groups in a single molecule, and therefore exhibit a high degree of stability and remarkable utility in concentrated electrolytic solutions. These compounds also show unusual chemical stability under prolonged contact with alkaline systems. Products made from the instant compounds have the following advantages: they possess good surface-active properties so that they can be used as hair shampoos over a wide pH range, for example from 3 to 10. In addition, they exhibit good detergent properties, i.e., they have the advantage of preventing the accumulation of electrostatic charges, impart a soft hand to the hair and permit ready combing. They are also very well tolerated by the skin and eyes and, therefore, do not cause any appreciable irritation thereto. The last-mentioned property also makes the instant amphoteric compounds useful when incorporated into a liquid bubble bath or when incorporated into a bar of washing soap.

The novel compounds of this invention have the following unexpected combination of properties: they are substantially non-irritating to the skin and to the eyes in those concentrations in which appreciable eye irritation is usually evidenced in ordinary shampoos; they are better foamers in average or hard water; they have good foam stability; they do not dull the hair when used for shampooing and consequently no special after rinse is required; they impart softness and manageability to hair which has been shampooed therewith in ordinary as well as hard water; and they may be used in shampoos and other cosmetics at pH values of 4.5–8.5.

The present amphoteric surfactants also show an advantage over the prior art as a result of improved lime soap dispersing properties. Also, such surfactants seemingly do not exhibit a pronounced isoelectric point where general surfaceactive and physical properties such as solubility, foaming, etc. are at a minimum.

Thus, it can be seen that the present invention provides for new compositions of matter and new articles of manufacture, such as surface-active compositions, toilet bars of soap, shampoos, bubble baths, etc., all of which, as is well known in the art, are susceptible to a wide variety of cosmetic applications.

DESCRIPTION OF THE PREFERRED EMBODIMENTS

Broadly speaking, the instant invention comprises the provision of amphoteric compounds that are characterized by the following generic formula.

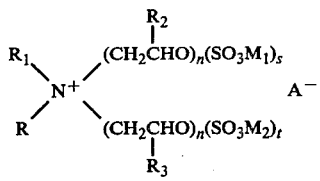

wherein R represents a $C_8$–$C_{14}$ aliphatic radical; $R_1$ represents a $C_1$–$C_4$ lower alkyl radical; $R_2$ and $R_3$ each represents H or $CH_3$; $M_1$ and $M_2$ represent cations of hydrogen, ammonium, alkyl ammonium, alkali metal, or an equivalent of alkaline earth metal; n is an integer having an average value of from 5 to 10; s and t can either be 0 or 1 but both cannot be simultaneously 0; and A represents an anionic radical such as hydroxide, halogen, sulfate, and alkyl sulfate.

Preferably R is a naturally occurring or synthetic alkyl group containing an average of 10-12 carbon atoms, and $M_1$ and $M_2$ when a metal cation can be Na, K, Mg, Ca, though preferably Na or K. $M_1$ or $M_2$ can also be hydrogen, ammonium or alkyl ammonium. A, when a halogen, may be chlorine, or bromine, preferably chlorine. When a sulfate, A may be an alkyl sulfate, preferably ethyl sulfate. In the most preferred embodiment R and $R_1$ are dissimilar, R being a long alkyl chain having an average carbon number 8-14, preferably 10-12, the other chain $R_1$ being a shorter alkyl chain having an average carbon number of 1-4. Also disclosed are methods of making same and uses therefor.

While not wishing to be bound or limited by any theory, it is nevertheless believed that perhaps the chief factor which determines (or at least largely influences) the irritation and foaming properties of the present amphoteric surfactants is the alkylene oxide content thereof. For example, when the present surfactants have less than 10 moles of ethylene oxide, they are high foaming materials but nonetheless are relatively irritating to the skin and eyes. However, when the present surfactants have more than 20 moles of ethylene oxide, they are virtually non-irritating but nevertheless they are poor foaming materials.

In accordance with the present invention, it has been found that an alkylene (e.g. ethylene or propylene) oxide content of between about 10 and 20 moles for the entire active surfactant composition is necessary in order to obtain both high foaming and virtually non-irritation of skin and eyes. Moreover, it is further necessary that R and $R_1$ have average carbon number ranges of $C_8$–$C_{14}$ and $C_1$–$C_4$ respectively to enhance or preserve the benefits of the present surfactants.

Furthermore, while the alkylene (e.g. ethylene or propylene) oxide content of the entire surfactant moiety constitutes about 10–20 moles, their distribution may be divided equally along the two main chains, e.g. 5 to 10 moles each, or unequally, e.g. 5 moles on one chain, 10 on the other or 10 moles on one chain and zero on the other. Likewise, there can be one or two separate quaternized, sulfated chains linked to the N+ moiety via the alkylene oxide moiety, and, accordingly, $M_1$ and $M_2$ can be the same or different consistent with this fact. In any event, all of this would be familiar chemistry to those skilled in the art.

The novel compounds of the instant invention may be prepared from a precursor material by first condensing an alkyl amine containing an average of 8 to 14 carbon atoms in its alkyl chain with an alkylene oxide in the presence of base so as to achieve an adduct having an average of 10–20 alkylene oxide units in the final compound. To produce the quaternized component, a conventional quaternizing agent is added thereto and the ethoxylated amine is thereafter quaternized. The quaternized ethoxylated amine is thereafter sulfated with a conventional sulfating agent so as to produce a quaternary sulfate.

The alkyl portion of the amine can be saturated or unsaturated, substituted or free from substitution. A pure source of alkyl amine to be employed may vary in carbon length from 8 to 14 carbon atoms; examples of pure saturated acids which could be used as precursors for such an amine are caproic, caprylic, capric, lauric and myristic. Any fatty acid or mixture of fatty acids whether pure or from impure sources may be employed as an amine precursor without departing from the spirit of the invention as long as it ends up containing from 8 to 14 carbon atoms in the resultant chain length, or the average number of carbon atoms in the resultant chain is from 8 to 14.

Preferred fatty acids are those contained in coconut oil. A typical coconut oil may contain fatty acids varying in length from 8 to 18 carbon atoms with an average of 12 carbon atoms. These fatty acids from coconut oil may be saturated or unsaturated.

The alkyl amines used in this invention may also be derived from the esters of the fatty acids without departing from the scope of the invention. The methyl or ethyl esters of the fatty acids may be easily condensed with polyamines or substituted polyamines, with ready removal of the methanol or ethanol that results during such condensation.

The fatty acid amine precursor is prepared in accordance with procedures well known in the art and, accordingly, that reaction and reaction product per se, form no part of the instant invention.

The thus-produced alkyl amine is then subjected to an ethoxylation reaction in accordance with procedures well known in the art, such as for example by reacting the amine with the required number of units of ethylene oxide, e.g. 10 to 20, to produce the ethoxylated amine employed in the instant invention. This oxyethylation reaction is well known in the art and fully described in U.S. Pat. No. 1,970,578 and in many other patents. The reaction is preferably carried out at elevated temperatures and pressures and may be catalyzed by quaternary hydroxides, amines, acids and/or coordinating type compounds although strong alkaline catalysts such as KOH or NaOH and the like are preferred because of the fewer by-products formed and the more easily controllable reaction conditions that accrue to their choice. Since the reaction is substantially quantitative, the molecular proportions of ethylene oxide and amine employed determine the average oxyethylene chain length of the resulting ethoxylated amine, although it will be understood that the product is a mixture of ethyoxylated amines of varying oxyethylene chain length. As stated above, sufficient ethylene oxide is employed to produce an ethyoxylated amine containing by weight about 55 to 80 percent of combined ethylene oxide and about 10 to 20 units of ethylene oxide. The optimum oxyethylene chain length will in any particular instance be determined mainly by the particular amine being oxyethylated, the particular detergent with which it is to be admixed, the hardness of the water in which the detergent is to be employed, the desired efficacy of the finished product for the particular application and the like.

Throughout the specification, the invention is described with reference to the sulfated, quaternized, alkoxylated amine, since the original amine as well as the alkoxylated form thereof are products known in the art. In any event, the alkoxylated amine may be used per se or the amine may be alkoxylated in accordance with procedures well known in the art.

The product of the invention is then conveniently prepared by reacting appropriate proportions of alkoxylated amine in the presence of hypophosphorous acid and a conventional quaternizing agent, such as diethylsulfate, the latter being present in the amounts of 50 to 100 mole %, preferably 90 to 100 mole %.

The alkoxylated amine starting materials, prepared by alkoxylating primary amines, have the structure $R-N-[CH_2-CH_2O)_nH]_2$, wherein R is an alkyl group as above described and n is a positive integer of from 5-10.

After completion of the reaction, the alkoxylated amine is thereafter submitted to treatment conducive to quaternization of the tertiary amino group, utilizing a conventional quaternizing agent. Thus, noting the above structural formula, suitable quaternizing agents include, dialkyl sulfates, e.g. dimethyl sulfate, diethyl sulfate, etc., alkyl sulfonic acids, e.g. methyl sulfonic acid, ethyl sulfonic acid, etc.; benzyl halides, e.g. benzyl chloride, benzyl bromide, benzyl iodide, etc.; alkyl halides, e.g. methyl chloride, etc. Accordingly, any conventional quarternizing agent (such as described in "Herstellung of Quartären Ammonium verbindungen" by J. Goerdeler in "Methoden der Organischen Chemie", 11/2. Georg Thieme Verlag (Stuttgart), 1958, pages 591–630) can be advantageously employed in the production of the quaternary alkoxylated amines used herein.

The above-quaternized composition is then preferably, but not necessarily, stripped of any unreacted quaternizing agent and thereafter reacted with a conventional sulfating agent so as to produce the quaternized, sulfated form thereof. Suitable sulfating agents include chlorosulfonic acid, sulfur trioxide, sulfamic acid, and sulfuric acid oleum.

In accordance with a preferred procedure of the present invention, the alkoxylated fatty amine and hypophosphorous acid (used as a catalyst) are mixed together and heated to about 90–100° C., preferably to about 30° C., and thereto there is added about 50 to 100 mole %, (i.e. about 0.5 to 1.0 mole per mole of alkoxylated amine) preferably about 90 to 100 mole %, of a suitable quaternizing agent and the mixture is thereafter heated so as to effect quaternization of the alkoxylated fatty acid amine. Any unreacted quaternizing agent may be stripped away at elevated temperature and under vacuum. The remaining product is thereafter cooled and there is slowly added thereto a suitable sulfating agent in amounts of about 10 to 200 mole %, (i.e. about 0.1 to 2.0 mole per mole of quaternized alkoxylated amine) preferably about 90 to 110 mole %, at temperatures of about 20 to 80° C., preferably about 30 to 40° C. If chlorosulfonic acid is used as the sulfating agent, the reaction mixture is bubbled with nitrogen at such temperature until a desired degree of chloride ion is reached, preferably about 0.01 to 1.0%. The sulfate ester is then drowned into water and base and there is thereafter obtained the surfactant solution containing the instant product.

For every mole of surfactant product, the amount of sulfate present therein can range from about 0.7 to about 2.0 moles, preferably 1.0 to 2.0 moles. The moiety R in such surfactant can be a naturally occurring or synthetic alkyl group; when derived from a pure source it can contain from 8 to 14 carbon atoms; when derived from an impure source or from a mixture of fatty acids, R can contain an average of about 8 to about 14 carbon atoms, preferably an average of about 10–12 carbon atoms. Those alkyls of higher carbon number than $C_{14}$ are poor foamers, and those below $C_8$ begin to lose their surfactant properties to a progressively increasing extent for values of $C_7$ and lower due to their corresponding increasing tendency to become insufficiently lipophilic as the values of C become smaller.

$R_1$ in the resultant surfactant can be $C_1-C_4$ lower alkyl, preferably $C_2H_5$.

$R_2$ and $R_3$ in the resultant surfactant can be ethylene oxide or propylene oxide, preferably ethylene oxide.

n in said surfactant product can range from 5 to 10, and preferably there are 15 moles of alkylene oxide, preferably ethylene oxide, in said product.

With respect to the $M_1$ or $M_2$ moiety in the resultant surfactant product, preferably at least one of these is $Na^+$ or $K^+$, the other being $H^+$. The anion A is preferably chloride.

When formulated into shampoos, the present amphoteric surfactants are so manufactured in accordance with conventional means and techniques. Typically included in such shampoo formulations, as a primary foamer and detergent, is a conventional lauryl sulfate, which may be present as a sodium salt, as an ether, as an ethanolamine, etc. The amount of lauryl sulfate present, on an active basis, is typically 5 wt % – 25 wt %, preferably 15 wt %. Also included in conventional shampoo formulations is a fatty acid dialkanolamide such as a fatty acid diethanolamide; this material, usually present in an amount ranging from about 1 wt % – 8 wt %, preferably 3–4 wt %, is utilized as a foam booster and foam stabilizer.

The amount of the present amphoteric surfactant to be utilized in the present formulations ranges from about 10 wt % to about 30 wt %, preferably 15 wt % – 30 wt %. Additionally, small amounts of other conventional materials can be present in the instant shampoo formulations. For example, typical perfumes can be present therein; as an aid to their solubilization in such formulations, up to a maximum of 5 wt % of glycerine or a glycol such as propylene or ethylene glycol can be used.

Apart from the foregoing ingredients, the balance of the final formulation is made up of water.

In the most preferred embodiment of this invention, relative to utility, the present amphoteric surfactants can be utilized as baby shampoos; for such utility they are blended with an anionic lauryl sulfate, as discussed above, the amount of the present amphoteric surfactant in said blend ranging from about 45 wt % to about 70 wt %.

The invention is further described with reference to the following representative compositions and processes for manufacture and varied use of the same; the examples are not, however, intended to limit the scope of this invention.

The nature of the invention may perhaps best be understood by recourse to the following detailed procedure for preparing typical members of the present sulfated, quaternized, ethoxylated amphoterics, all parts, proportions and percentages in the following examples as well as in the appended claims being by weight unless indicated otherwise.

EXAMPLE I

Charge into a 1-liter flask, equipped with an agitator, thermometer and gas inlet, 320 parts (0.5 mole) of cocoamine + 10EO (where EO is, of course, ethylene oxide) and 2 parts of 50% hypophosphorous acid. Dry the mixture under vacuum (10-15 mm.) at 90-100° C. Cool under dry nitrogen to 40-50° C. and add 80 parts (0.52 mole) of diethyl sulfate at 40-50° C. over two hours.

Strip any unreacted diethyl sulfate at 85-90° C. under vacuum. Cool to 30-40° C and add slowly over 2 hours, with a nitrogen jet dispersing the droplets, 60 parts (0.52 mole) of chlorosulfonic acid at 30-40° C. Continue nitrogen bubbling for six hours at 30-40° C., until the Cl is 0.5%. The sulfate ester is then drowned in 150 parts of water and 51 parts of 50% caustic to a pH of 7.3. There is obtained 615 g. of surfactant solution containing 440 parts active material. This represents a 98% yield.

EXAMPLE II

Operating as in Example I, charge 430 parts of cocoamine + 15EO (0.5 mole), 2 parts of hypophosphorous acid and dry under vacuum. At 40-50° C., add 80 parts of diethyl sulfate (0.52 mole) and hold 2 hours at 40-50° C. Distill unreacted volatiles at 85-90° C. under 2 mm. vacuum and then add at 40° C., 60 parts chlorosulfonic acid (0.52 mole) with a nitrogen jet to disperse the acid. Continue nitrogen purging for six hours and then drown in 150 parts water and 50 parts of 50% caustic. The pH is 7.3. There is obtained 713 g. of amphoteric surfactant solution containing 540 g. active material representing a 98% yield, said active material being illustrative of the most preferred embodiment of the surfactants of this invention and being characterized, as will be shown below, by high foaming and essentially non-irritating properties.

EXAMPLE III

In accordance with the procedure of Example I, charge 600 parts (0.25 mole) of cocoamine + 50EO and 2 parts of 50% hypophosphorous acid. After drying under vacuum, 40 parts (0.26 mole) of diethyl sulfate are added at 40-50° C over two hours. After an additional two hours at temperature, the reaction mixture is stripped at 85-90° C. under vacuum and 30 parts (0.26 mole) of chlorosulfonic acid is added with nitrogen dispersion at 40° C. Six hours of nitrogen bubbling reduced the Cl$^-$ to 0.07%. The crude acid is drowned in 150 parts water and 28.5 parts 50% caustic to yield 810 parts of 80.5% active surfactant solution of pH 7.5. This product is found to be characterized, as will be shown below, by poor foaming properties but also by good low-irritation properties.

EXAMPLE IV

In accordance with the procedure of Example I, 315 parts of cocoamine + 5EO (Armak's Ethomeen C-15) and 2 parts of 50% hypophosphorous acid are dried and reacted with 125 parts of diethyl sulfate. The resulting quaternary is reacted with 88 parts of chlorosulfonic acid and purged with inert gas to reduce the Cl$^-$ content to 0.2%. The quaternized sulfate ester is drowned in 150 parts water and 70 parts 50% caustic to yield 653 parts of 70.8% active surfactant solution at a pH of 7.6. The resultant product is found to possess good foaming properties but is deficient because it also displays high irritation capabilities.

EXAMPLE V

A conventional shampoo formulation, in terms of having average foaming and non-irritation properties, can be prepared in accordance with the following:

| Shampoo Formulation | | |
|---|---|---|
| Ingredients | | % By Weight |
| Sodium sulfate of cocoamine + 10EO diethyl sulfate | | 20.0 (solids) |
| Myristyl amine oxide (30% solids) | | 5.0 |
| Water | | 75.0 |
| | | 100.0 |

The product prepared above was evaluated for Ross Miles foaming in soft and hard water, stability (overnight) at 0.° C., surface tension and pH.

TABLE I

| Results of Experimental Amphoteric Shampoo |
|---|
| FOAM HT - mm .25% at 30° C. |
|   in distilled water -    160 (initial)    140(after 5 min.) |
| FOAM HT - mm .25% at 30° C. in |
|   ppm CaCO$_3$   (hard water) - 175 (initial)   150(after 5 min.) |
| Clarity - 12 hrs. at 0° C. - clear and stable |
| $\gamma s^{(1)}$ dynes cm. .25% solution at 25° C. - 31.6 |
|                     pH (as is) - 8.0 |

As shown above, the foregoing shampoo formulations demonstrate that shampoo formulations can be prepared which: foam well in both hard and soft water. The $\gamma s$ (surface tension) of a 0.25% solution is 31.6 dynes/cm at 25° C. well within the acceptable level for a high quality shampoo which should lower the $\gamma s$ to less than 40 dynes/cm at 0.1 to 0.25% in water. The same properties are exhibited using compounds containing 5-15 and 20 moles of ethylene oxide.

EXAMPLE VI

In order to demonstrate further the significance of the alkylene (e.g. ethylene or propylene) oxide content of the present amphoteric surfactants, particularly with respect to foaming and eye and skin irritation, samples of an amphoteric surfactant of the following description were prepared: R = alkyl derived from a coconut fatty acid; $R_1 = C_2H_5$; $R_2$ and $R_3$ = H; total $OSO_3^{31}$ = 1.0 mole; $M^+(M_1$ and $M_2) = Na^+$; $A^- = C_2H_5SO_4$; and n = 5, 10, 15, and 20.

Samples of this description were then utilized in the following tests: (a) Primary Skin Irritation; (b) Primary Eye Irritation; and (c) Foaming. The procedure followed for (a) the Primary Skin Irritation test was that performed on albino rabbits in accordance with the method described in Section 181.11, Federal Register, Vol. 26, No. 155, page 7336, Aug. 12, 1961. The procedure followed for (b) the Primary Eye Irritation test was that also performed on albino rabbits in accordance with the method described in Section 191.12 (a) (1) and (2) of the Final Order, Federal Register, Vol. 29, No. 182, page 13009, Sept. 17, 1964. The procedure followed for (c) the Foaming test was that employed in the Ross and Miles Foamometer Test set forth by J. Ross and G. D. Miles in "Oil and Soap", Vol. 18, pages 99–102 (1941).

The results of Tests (a)–(c) are set forth below in Tables II–IV, respectively.

TABLE II

| PRIMARY SKIN IRRITATION | | | |
|---|---|---|---|
| Compound | Percent Solids | Irritation Index | Comments |
| Half sulfate ester of cocoamine + 5 EO diethyl sulfate | 70.8 | 4.12 | Mild edema, moderate erythema to both intact & abraided skin. |
| Half sulfate ester of cocoamine + 15 EO diethyl sulfate | 75.5 | 1.17 | No edema, mild erythema. |
| Half sulfate ester of cocoamine + 20 EO diethyl sulfate | 77.5 | 0.58 | No edema, mild transient erythema. |

LEGEND-IRRITATION INDEX
0–2 Mild
2.5–5.5 Moderate
6–Above Severe

As shwon in Table II the amphoteric surfactant exhibited decreased skin irritation with increasing ethylene oxide in the molecule. Hence, none of the three compounds would require precautionary labeling for skin irritation at the concentrations tested.

TABLE III

| PRIMARY EYE IRRITATION | | | |
|---|---|---|---|
| Compound | Percent Solids | Positive Reaction No. Animals/No. Tested | |
| Half sulfate ester of cocoamine + 5 EO diethyl sulfate | 70.8 | 1/1 | Severe occular irritant, corneal opacity after the 7th day of observation. |
| Half sulfate ester of cocoamine + 15 EO diethyl sulfate | 75.5 | 4/6 | Mild transient conjunctival effects which clear by the second and third day of observation |
| Half sulfate ester of cocoamine + 20 EO diethyl sulfate | 77.5 | 0/6 | Compound is not an occular irritant at 77.5% solids |

The foregoing skin and eye data obtained on the half sulfate ester of cocoamine and 15 EO diethyl sulfate showed the product to be mild and about equal to the 20 ED adduct.

TABLE IV

Foaming Properties Ross Miles - 35° C. (Initial/After 5 Min) Foam HT In MM

| Amphoteric Half Sulfate Ester Cocoamine + (X)EO | Conc. | Soft Water | 200 ppm CaCO$_3$ |
|---|---|---|---|
| +5 EO | .05 | 45/20 | 60/50 |
|  | .10 | 50/25 | 80/60 |
|  | .50 | 170/40 | 160/20 |
|  | 1.00 | 195/25 | 175/0 |
| +10 EO | .05 | 80/65 | 140/110 |
|  | .10 | 130/30 | 150/120 |
|  | .50 | 180/90 | 175/50 |
|  | 1.00 | 195/90 | 190/65 |
| +15 EO | .05 | 95/80 | 120/90 |
|  | .10 | 115/90 | 130/70 |
|  | .50 | 165/70 | 160/60 |
|  | 1.00 | 175/20 | 175/25 |
| +20 EO | .05 | 45/30 | — |
|  | .10 | 75/20 | 80/0 |
|  | .50 | 125/5 | 55/0 |
|  | 1.00 | 140/0 | 95/5 |

As shown in Table IV, the foaming properties of the 5, 10, 15 and 20 mole EO adducts were tested in both soft and hard water. In general, these compounds are moderately high unstable foamers with optimum EO content at the 10 and 15 mole level, and foaming is not adversely affected by hard water for both the latter compounds. With 20 moles, however, of EO, initial foam, foam stability, and hard water foaming were slightly imparied. The 20 EO adduct was inferior to the 10 and 15 mole products at the 0.05 and 0.1% levels in both soft and hard water.

EXAMPLE VII

The lime soap dispersion index (Journal American Oil Chem. Soc., Vol. XXVII-88, 1950) of several of the above amphoterics is determined and compared to a commercial amphoteric control (Miranol C2M) normally used in shampoo and cosmetic products. The results appear in Table V. The lower the number the better the lime soap dispersant properties.

TABLE V

| Lime Soap Dispersion Index | |
|---|---|
| Product | Lime Soap Dispersion Index |
| Sodium sulfate of cocoamine +15EO diethyl sulfate | 2.5–5.0 |
| Sodium sulfate of cocoamine +10EO benzyl chloride | 2.5–5.0 |
| Miranol C2M - conc. - (Imidazoline type - the Miranol Corp.) | 80 |

EXAMPLES VIII–X

The following concentrates (VIII–X) were prepared using the experimental amphoterics of Example III, with varying degrees of ethoxylation and were evaluated as liquid concentrates for use in a bubble bath.

TABLE VI

| Liquid Bubble Bath Concentrates | | | |
|---|---|---|---|
|  | All by Weight % | | |
| Ingredient | VIII | IX | X |
| VIII-Sodium sulfate of cocoamine | | | |

TABLE VI-continued

| | Liquid Bubble Bath Concentrates | | |
|---|---|---|---|
| | All by Weight % | | |
| Ingredient | VIII | IX | X |
| + 10 EO diethyl sulfate (solids) | 20.0 | — | — |
| IX-Same as (VIII) with 15EO (solids) | — | 20.0 | — |
| X-Same as (VIII with 20EO (solids) | — | — | 20.0 |
| Coconut diethanolamide | 5.0 | 5.0 | 5.0 |
| Water- | 75.0 | 75.0 | 75.0 |
| Totals | 100.0 | 100.0 | 100.0 |

All of these formulations foamed well in both hard and soft water and in the presence of soap and hard water. The latter is a major criteria for a high quality bubble bath. The results are shown in TABLE VII.

TABLE VII

Ross Miles Foam Tests on Bubble Bath Conc. 1–4 of Examples 8–10

| | PPMCaCO₃ | | | Foam HT in MM(Initial/after 5 min.) | | |
|---|---|---|---|---|---|---|
| Percent | Water | Temp. | % | Formulation Number | | |
| Concentration | Hardness | °C | Soap | 1 | 2 | 3 |
| (1) | .25 | 0 | 30 | 0 | 175 155 | 180 155 | 185 165 |
| (2) | .25 | 200 | 30 | 0 | 185 160 | 190 165 | 190 170 |
| (3) | .025 | 200 | 37 | .5 | 205 180 | 215 175 | 210 175 |
| (4) | .125 | 200 | 37 | .5 | 195 165 | 185 160 | 205 180 |

All of the above concentrates were stable to overnight refrigeration and also to one cycle of freeze/thaw.

EXAMPLE XI

Toilet bars of the soap syndet and syndet types with lime soap dispersant, emollient and antibacterial properties may be prepared as shown in TABLE VIII.

Various fillers or diluents may be advantageously used in the above soap composition to lower its cost. Clay, hydrogenated tallow, powdered polyvinyl chloride resin, paraffin wax, starch and stearic acid are examples of such materials. These, of course, are preferably used in limited amounts to avoid affecting substantially the properties of the bar, such as lathering power and surface slipperiness. Limited amounts (e.g. below 10%) of certain fillers or diluents such as starch and stearic acid actually enhance the surface slipperiness of the bar. Some fillers, such as glycerine, polyglycerine (e.g. of degree of polymerization of about 6), sugar, pectin, gelatin, finely divided silica, in limited amounts (e.g. less than 15%) inhibit the cracking of the bars which may occur when the bars dry out after use.

EXAMPLE XII

Herebelow are included representative formulations of four different (A-D) baby shampoo formulations containing, as active ingredient, the 15 EO material of Example VI which would be of commercial utility. The compositions of each of these are set forth below in TABLE IX.

TABLE IX

| Formulation | A Baby Shampoo High Foaming | | B Baby Shampoo High Foaming Tangle-Free | | C Baby Shampoo Luxury Foam | | D Economy Baby Shampoo | |
|---|---|---|---|---|---|---|---|---|
| Ingredients | % | % Active | % | % Active | % | % Active | % | % Active |
| VI-15 EO amphoteric 75% | 8.0 | 6.0 | 8.0 | 6.0 | 8.0 | 6.0 | 3.0 | 2.25 |
| Miranol CM (imidazoline type) | 15.0 | 5.7 | 15.0 | 5.7 | 15.0 | 5.7 | 20.0 | 7.6 |
| "Igepon ®" TC-42 anionic 24% (GAF) | — | — | — | — | 15.0 | 3.6 | — | — |
| "Maprofix" ES sodium lauryl ether sulfate 30% (Onyx) | 13.5 | 4.0 | 13.5 | 4.0 | — | — | 15.0 | 4.5 |
| PEG (polyethylene glycol) 6000 distearate (Armak) | 2.8 | 2.8 | 3.1 | 3.1 | 3.3 | 3.3 | 1.0 | 1.0 |
| "Gafquat ®" 734 quaternized vinylpyrrolidone polymer 50% (GAF) | — | — | 2.0 | 1.0 | — | — | — | — |
| Sulfuric Acid | q.s. to pH6.7 | | q.s. to pH7.4 | | q.s. to pH6.7 | | q.s. to pH7.4 | |
| Water | q.s. to 100 | | q.s. to 100 | | q.s. to 100 | | q.s. to 100 | |

TABLE VIII

| | All parts by wt. % | | |
|---|---|---|---|
| | 1 | 2 | 3 |
| Paraffin Wax | — | 5–15 | 5–15 |
| Amphoteric Surfactant | 5–15 | 20–50 | 20–50 |
| Tallow Coconut Oil Soap | 60–80 | — | — |
| Stearic Acid | 0–10 | 0–20 | 0–20 |
| Alkyl dimethyl benzyl ammonium halide | — | .5–1.0 | — |
| Talc | — | 20–60 | 20–60 |
| Water | to 100% | to 100% | to 100% |

EXAMPLE XIII

In this Example, the 15 EO material of Example VI was formulated into a shampoo and subjected to a comparative study with a leading baby shampoo, i.e. Johnson and Johnson Baby Shampoo. The results of this study are summarized below:

Rabbit Eye Irritation Comparison Summary

| Shampoo A* vs. J&J Baby Shampoo | |
|---|---|
| Procedure: Study performed on 6 Albino rabbits according to method described in 16 CFR 1500.42. | Study performed on 6 Albino rabbits according to method described in |

-continued

| Shampoo A* vs. J&J Baby Shampoo | |
|---|---|
| Results: Test material produced no corneal or iridial effects and only very mild transient conjunctival effects in two rabbits which cleared by the second day of observation. | 16 CFR 1500.42. Test material produced no corneal, iridial, or conjunctival effects in any of the animals. |
| Conclusion: Sample as tested in rabbits is not an eye irritant in accordance with the criteria specified in 16 CFR 1500.3. | Sample as tested in rabbits is not an eye irritant in accordance with the criteria specified in 16 CFR 1500.3. |

RABBIT EYE IRRITATION DATA

| Positive Reactions | DAY 1 | | DAY 2 | | DAY 3 | |
|---|---|---|---|---|---|---|
| | VI-15EO | J & J Shampoo | VI-15EO | J & J Shampoo | VI-15EO | J & J Shampoo |
| CORNEA | | | | | | |
| -Opacity | 0 | 0 | 0 | 0 | 0 | 0 |
| -Area | 0 | 0 | 0 | 0 | 0 | 0 |
| IRIS | 0 | 0 | 0 | 0 | 0 | 0 |
| CONJUNC-TIVA | | | | | | |
| -Redness | 2/6[(1)] | 0 | 0 | 0 | 0 | 0 |
| -Chemosis | 0[(2)] | 0 | 0 | 0 | 0 | 0 |
| -Discharge | 0 | 0 | 0 | 0 | 0 | 0 |

[(1)]Slight redness on the first day was observed in only 2 out of 6 animals which cleared by the second day.
[(2)]Zero indicates no effect.
*Indicates the source of this shampoo is the shampoo having the composition of the Formulation A, as set forth in Table IX above.

EXAMPLE XIV

Herebelow are included further representative formulations of three additional shampoo formulations that characterize the present invention and contain, as active ingredient, the 15 EO material of Example VI. The compositions of each of these formulations are set forth below in Tables X – XII, respectively.

TABLE X

| Clear Baby Shampoo - Ultra Mild | | |
|---|---|---|
| Ingredients | % | % Active |
| VI-15EO amphoteric, 75% | 12.0 | 9.0 |
| "Sipon" ES sodium lauryl ether sulfate, 27% (Alcolac) | 18.5 | 5.0 |
| "Aromox" C/12W di(hydroxyethyl)-cocoamine oxide, 40% (Armak) | 7.5 | 3.0 |
| "Gafamide ®" CDD-518 foam booster, 100% (GAF) | 1.0 | |
| PEG 6000 Distearate (Armak) | 3.5 | |
| Citric Acid | 0.52 | |
| Water (Distilled) | q.s. to 100 | |

TABLE XI

| Clear Adult/Baby Shampoo - Mild & Tangle-Free | | |
|---|---|---|
| Ingredients | % | % Active |
| VI-15EO amphoteric, 75% | 12.0 | 9.0 |
| "Sipon" ES sodium lauryl ether sulfate 27% (Alcolac) | 18.5 | 5.0 |
| "Aromax" C/12W di(hydroxyethyl)-cocoamine oxide, 40% (Armak) | 7.5 | 3.0 |
| "Gafamide"CDD-518 foam booster, 100% (GAF) | 1.0 | |
| PEG 6000 Distearate (Armak) | 3.3 | |
| "Gafquat®" 755 quaternized vinyl-pyrrolidone polymer, 20% (GAF) | 2.5 | 0.5 |
| Citric Acid | q.s. to pH 6.5 | |
| Water (Distilled) | q.s. to 100 | |

TABLE XII

| General Purpose Shampoo - High Foaming | | |
|---|---|---|
| Ingredients | % | % Active |
| VI-15EO amphoteric, 75% | 15.0 | 11.25 |
| "Igepon®" TC-42 anionic, 24 % (GAF) | 20.0 | 4.8 |
| PEG 6000 Distearate (Armak) | 3.0 | |
| "Amonyx" LO lauryl dimethylamine oxide, 30% (Onyx) | 10.0 | 3.0 |
| Citric Acid | q.s. to pH 6.5 | |
| Water (Distilled) | q.s. to 100 | |

EXAMPLE XV

In this example, the composition of a typical soap-synthetic detergent ("Soap-Syndet") shampoo formulation is set forth in Table XIII below. This formulation contains the 15 EO material of Example VI as active ingredient.

TABLE XIII

| SOAP-SYNDET SHAMPOO | |
|---|---|
| COCONUT FATTY ACIDS | 3.0% |
| OLEIC ACID | 7.0% |
| TRIETHANOLAMINE (85%) | 6.5% |
| LAURIC DIETHANOLAMIDE | 2.0% |
| VI-15 EO | 4.0% |
| SODIUM LAURYL 3 EO SULFATE | 35.0% |
| DISTILLED WATER, q.s. | 100.0% |
| pH | 7.8 |
| VISCOSITY | 2,000 cps |
| CLEAR TO 0° C. | |
| SOAP SYNDET RATIO 53/47 | |

Additional features of the above-outlined invention include: foam formation without water pressure, foam regeneration, foam compatibility with soap and soap foam, sequestration properties, solution compatibility with very high quantities of electrolytes and/or alkalies, compatibility with quaternary germicides, germicidal, germistatic, fungicidal, and fungistatic properties, deodorizing properties, and non "drying" properties on the skin. It is obvious that numerous changes and modifications can be made in the invention without departing from the spirit and scope thereof and all such obvious modifications are considered to be within the scope of the invention.

What we claim is:

1. A method comprising washing human hair and skin with an aqueous composition containing an effective washing amount of an amphoteric surface active compound of the formula:

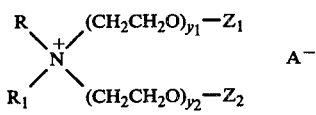

wherein R is $C_{8-14}$ alkyl, $R_1$ is $C_{1-2}$ alkyl or benzyl;

$y_1$ and $y_2$ are each integers, the sum of which ranges from about 5 to about 50;

$Z_1$ is, with the bonded O atom, a sulfate ester group in free acid form or in the form of its sodium, potassium, magnesium or calcium salt, $Z_2$ is H or $Z_1$; and A is a halide, sulfate or $C_{1-2}$ alkyl sulfate anion; or a mixture of such compounds.

2. A method as defined in claim 1 in which $Z_1$ is in the form of the Na salt.

3. A method as defined in claim 1 wherein $R_1$ is ethyl and A is ethyl sulfate.

4. A method as defined in claim 1 wherein $R_1$ is benzyl and A is a chlorine anion.

5. A method as defined in claim 1 wherein the sum of $y_1$ and $y_2$ is about 10 to about 20.

6. A method as defined in claim 5 wherein R is derived from cocoamine, $R_1$ is ethyl, $Z_1$ is in the form of the Na salt, and A is ethyl sulfate.

7. A method as defined in claim 1 wherein R is derived from cocoamine.

8. A method as defined in claim 1 wherein said composition is an aqueous solution of a shampoo formulation containing 20% of said compound and 1.5% of long chain amine oxide.

9. A method as defined in claim 1 wherein said composition is an aqueous solution of a bubble bath concentrate containing 20% of said compound and 5% of coconut diethanolamide.

10. A method as defined in claim 1 wherein said composition is derived from a solid bar containing 5–15% of said compound, 60–80% of tallow coconut oil soap and 0–10% of stearic acid.

11. A method as defined in claim 1 wherein said composition is derived from a solid bar containing 20–50% of said compound, 5–15% of paraffin wax, 0–20% of stearic acid, 0.5–1.0% of alkyl dimethyl benzyl ammonium cloride, and 20–60% of talc.

12. A method as defined in claim 1 wherein said composition is derived from a solid bar containing 20–50% of said agent, 5–15% of paraffin wax, 0–20% of stearic acid, and 20–60% of talc.

13. A method as defined in claim 1 wherein said compound is prepared by reacting 1 mole of the reaction product of 1 mole of an organic amine of the formula $RNH_2$ with about 5 to about 50 moles of ethylene oxide, with 0.5 to 1.0 mole of a quarternizing agent of the formula $R_1A$, and then reacting the reslulting quarternized polyethoxylated amine with about 0.1 to 2.0 mole of a sulfating agent selected from the group consisting of chlorosulfonic acid, sulfur trioxide, sulfamic acid and sulfuric acid oleum.

* * * * *